(12) United States Patent
Fullen et al.

(10) Patent No.: US 6,804,571 B2
(45) Date of Patent: Oct. 12, 2004

(54) METHOD FOR COMPUTER AIDED ORTHOTIC INLAY FABRICATION

(75) Inventors: Jeryl G. Fullen, Salina, KS (US); George R. Fullen, Littleton, CO (US)

(73) Assignee: Fullen Systems, LLC, Salina, KS (US)

( * ) Notice: Subject to any disclaimer, the term of this patent is extended or adjusted under 35 U.S.C. 154(b) by 383 days.

(21) Appl. No.: 09/808,453

(22) Filed: Mar. 13, 2001

(65) Prior Publication Data

US 2001/0047246 A1 Nov. 29, 2001

Related U.S. Application Data

(60) Provisional application No. 60/188,791, filed on Mar. 13, 2000.

(51) Int. Cl.$^7$ .................... G06F 19/00; A61B 5/103; A61F 5/14
(52) U.S. Cl. ................ 700/118; 700/98; 36/140; 73/172; 600/592; 702/33
(58) Field of Search .................. 702/33, 167; 73/172, 73/179; 36/1, 136, 140, 145, 137; 600/592; 382/154; 700/96, 97, 98, 117, 118

(56) References Cited

U.S. PATENT DOCUMENTS

| | | | |
|---|---|---|---|
| 3,791,375 A | 2/1974 | Pfeiffer | 600/592 |
| 3,974,491 A | 8/1976 | Sipe | 340/572 |
| 4,517,696 A | 5/1985 | Schartz | 12/1 R |
| 4,647,918 A | 3/1987 | Goforth | 340/573.1 |
| 4,734,034 A | 3/1988 | Maness et al. | 433/68 |
| 4,745,930 A | 5/1988 | Confer | 600/592 |
| 4,813,436 A | 3/1989 | Au | 600/592 |
| 4,856,993 A | 8/1989 | Maness et al. | 433/68 |
| 4,862,743 A | 9/1989 | Seitz | 73/172 |
| 4,876,758 A | 10/1989 | Rolloff et al. | 12/142 N |
| 5,033,291 A | 7/1991 | Podoloff et al. | 73/172 |
| 5,079,949 A | 1/1992 | Tamori | 73/172 |
| 5,088,503 A | 2/1992 | Serts | 600/592 |
| 5,237,520 A * | 8/1993 | White | 382/154 |
| 5,253,656 A | 10/1993 | Rincoe et al. | 600/595 |
| 5,323,650 A | 6/1994 | Fullen et al. | 73/172 |
| 5,394,626 A * | 3/1995 | Brown | 36/99 |
| 5,449,002 A * | 9/1995 | Goldman | 600/592 |
| 5,449,256 A * | 9/1995 | Sundman | 409/134 |
| 5,640,779 A | 6/1997 | Rolloff et al. | 33/514.2 |
| 5,678,448 A | 10/1997 | Fullen et al. | 73/172 |
| 5,790,256 A * | 8/1998 | Brown et al. | 356/613 |
| 6,000,082 A * | 12/1999 | Nguyen | 12/142 N |
| 6,141,889 A | 11/2000 | Baum | 36/140 |
| 6,195,921 B1 | 3/2001 | Truong | 36/136 |
| 6,360,597 B1 * | 3/2002 | Hubbard, Jr. | 73/172 |
| 6,463,351 B1 * | 10/2002 | Clynch | 700/163 |

FOREIGN PATENT DOCUMENTS

| | | |
|---|---|---|
| DE | 26 56 864 A1 | 5/1978 |
| DE | 3631 923 A1 | 3/1988 |

OTHER PUBLICATIONS

Endicott, Donald et al., "Leg Load Warning System for the Orthopedically Handicapped," *Medical and Biological Engineering*, May 1974.

Miyazaki, S. & Iwakura, H., "Foot–Force Measuring Device for Clinical Assessment of Pathological Gait," *Medical and Biological Engineering and Computing* Jul. 1978.

Spolek, G. A. & Lippert, F. G., "An Instrumented Shoe A Portable Force Measuring Device," *J. Biomechanics* (Great Britain, Jun. 1976).

Purbrick, John A., "A Force Transducer Employing Conducive Silicone Rubber," First Robot Vision and Sensors Conferences, Stratford–on–Avon, England, Apr. 1981.

* cited by examiner

*Primary Examiner*—Paul Rodriguez
(74) *Attorney, Agent, or Firm*—Sheridan Ross P.C.

(57) ABSTRACT

The present invention relates to a process for determining the magnitude and distribution of forces on a foot during ambulation and utilizing this data in combination with a plurality of other factors to create an orthotic inlay with an automated inlay fabricating machine.

24 Claims, 14 Drawing Sheets

METHOD FOR COMPUTER AIDED ORTHOTIC INLAY FABRICATION

This application claims priority of U.S. provisional patent application Ser. No. 60/188,791, having a filing date of Mar. 13, 2000, and is incorporated herein in its entirety by reference.

FIELD OF THE INVENTION

The present invention relates to an apparatus and method for measuring the forces and distribution of forces on a user's foot and utilizing this data in combination with other factors to manufacture a custom designed orthotic inlay with an automated fabrication machine.

BACKGROUND OF THE INVENTION

Footwear has been utilized by mankind for thousands of years for protection from rough terrain, thermal extremes, and other hazards. Although primarily utilitarian in nature, footwear construction and design are often influenced by custom and aesthetics. In recent times, the design of footwear has focused more on achieving maximum comfort in general and specialized construction for athletic uses.

Regardless of the protection and other benefits of footwear, they also are frequently a source of discomfort and, sometimes, trauma. Although footwear manufacturers often attempt to produce comfortable footwear, manufacturing practice and distribution methods effectively limit the range of sizes and shapes available to the purchaser. Women's high heeled shoes, for example, are frequently uncomfortable and can lead to acquired problems of the foot. Even regular Oxford style footwear with a standard heel and adequate room for the foot is frequently uncomfortable. This is due to the limited size and shape of footwear available for a limitless variety of human foot sizes and shapes. There are frequently size differences between the feet of the same individual and even the same foot between the heel and forefoot. For example, the right foot may require a size 10-medium shoe while the left requires a size nine. Furthermore, the individual's right heel may be smaller than the predicated standard forefoot to heel width for the size 10-medium shoe. Since footwear is sold in pairs of the same size (length and width), the general rule is to obtain the largest size that will fit both feet and hope for the best. Since neither foot, in the above example, is properly fitted, abnormal loads and movement within the footwear during ambulation can be anticipated.

Another issue not addressed by footwear manufacturers and not readily appreciated by the consumer but which has a direct bearing on comfort is the concept of body weight to foot size ratio. For example, an inlay specification for a person weighing 140 pounds and wearing a size 10 shoe compared to another individual who weighs 200 pounds with the same size footwear is significantly different.

Producing comfortable footwear is made more difficult by the fact that the structure and shape of both the foot and footwear changes during movement which can generate complex plantar pressures. Local areas of high plantar pressure frequently causes pain forcing an individual to adopt unusual ambulation patterns which may, in turn, cause secondary problems in the foot, leg or back. Prolonged areas of high local pressure can result in painful blisters and skin thickening or callus formation. When this is coupled with loss of protective sensation, such as in diabetics, prolonged abnormal pressures can result in ulceration, bone infection and ultimately, amputation. The measurement of the magnitude and distribution of forces present on the plantar surface of the patient's foot during ambulation is described in detail in the Applicants' U.S. Pat. Nos. 5,678,448 and 5,323,650, which are incorporated herein in their entirety by reference.

Foot problems increase with age and may include gradual destruction, over time, of the protective fat pads located under the bony heel and under each of the toe bases. This coupled with arthritic changes in the foot results in a less adaptable foot during ambulation subject to increasing discomfort and secondary changes to include limited joint motion and muscle imbalance.

Footwear manufacturers, depending on intended use, vary sole rigidity which tends to disperse high local pressures generated by sharp objects. They generally provide a thin, inadequate, generic pad for the plantar foot for esthetics. From the above discussion, it should be obvious that a specifically designed interface (inlay) between the plantar foot and footwear is needed to match the unique foot to the generic footwear which objectively address the above issues.

Recognizing the need for an interface between the plantar foot and footwear is, of course, not new. In 1865, Everett H. Dunbar designed the leather lift. In 1905, Dr. Royal Whitman developed the first medical inlay referred to as the whittman plate. In 1910, Dr. William Scholl commercialized the first arch support, the Foot Eazer. Custom inlays (orthotics) began to be developed during the 1930's but it wasn't until the 1980's that semi-automated fabrication systems began to appear. These systems generally automate the process of making the positive mold then resort to traditional inlay fabrication techniques.

Current custom inlay design is based on the shape of the bottom of the foot and to a lessor extent, the inside shape of footwear. Traditionally, a cast mold is made by pouring plaster into a foam impression of the planter foot. Various moldable materials are pressure and/or heat fitted to the cast mold. Highly skilled inlay fabricators (podiatrist, orthotist or pedorthist) then fit the molded inlay product to the foot and shoe. Depending on the skill of the fabricator, an inlay can be fitted to achieve a fairly high degree of comfort based on trial and error methods. Unfortunately, these custom inlays or orthotics require 3 to 4 hours of labor over several days and multiple return visits by the wearer to make the necessary adjustments. Custom inlays are, therefore, time intensive to fabricate, expensive and are at best only an educated estimate of the ideal fit. The effects of changes in the foot and footwear shape during ambulation are ignored, as well as the actual forces which are being exerted on the foot.

An automated method as taught by Schartz (U.S. Pat. No. 4,517,696) and Rolloff (U.S. Pat. Nos. 4,876,758 and 5,640,779) uses a device which generates a numeric foot shape description by use of closely spaced pins pushing against the plantar surface of the foot while the individual is standing or seated. The foot being measured rests on a firm flat platform, and the pins are pushed against the foot with varying pressure, distorting the foot in the process. The displacement of each pin is separately expressed as a number. Thus, this group of numbers represents the shape of the foot. This numeric information is then suitably processed and used as input to a numeric controlled machine to produce inlays. This method is flawed in several respects. First, it modifies the actual shape of the foot during measurement. Second, the process only accumulates data on a stationary foot as opposed to measurements on a foot in motion. These methods do not provide true pressure mapping of the plantar foot.

The fabrication component of this method uses pre-formed blanks and only mills the top side. The tool path is a first traverse of the perimeter of the milled area with subsequent traverses offset to the center of the work piece. This is a traditional fabrication process used for milling a rigid work piece. However, it is an inferior process for use with soft materials due to problems associated with holding the work piece and debris collection issues. Further, the use of pre-formed blanks creates an inventory problem because each shoe brand, style, and size is a separate stock item.

Another process requires that an individual take several steps while barefoot on a capacitive matrix force plate, as taught by U.S. Pat. No. 5,088,503 to Serts. A digital pressure map of the plantar foot is developed and augmented by fabricator input. The resultant prescription file is sent by modem to a central facility where a semi-rigid orthotic inlay is manually fabricated. This process has several significant limitations. There is no in-shoe pressure data obtained, the entire ambulation cycle is not studied, the sample size is limited to just a few steps on a force plate and the very process of stepping on a force plate at a specific location affects the measurements and renders them invalid for use in developing an inlay specification.

A non-automated method has further been utilized by inserting a pre-heated (softened) thermoplastic material between the footwear and the user's plantar foot. When the individual stands, the soft material migrates from any high pressure area to a low pressure area. After cooling, the insert retains the new shape. This inlay functions to hold the plantar foot in a preset neutral position but achieves very little plantar pressure re-distribution. Again, only the non-dynamic stance phase of foot pressure is addressed, i.e. non ambulatory, and represents, at best, a holding form for the foot.

There is thus a significant need for an orthotic inlay which reduces excessive differential plantar pressures, provides a significant reduction in fabrication time, can be designed to match the foot to specific footwear not only while standing but also while engaged in any form of ambulation, and can be produced in a manner to reduce fabrication error and provide a means to objectively document the post-fit plantar pressures. An apparatus and method describing such a system is described hereinbelow.

SUMMARY OF THE INVENTION

It is thus one object of the present invention to provide an improved method for creating an orthotic inlay by utilizing force distribution measurements and generating an optimal force distribution profile. These force distribution measurements are obtained during the ambulatory functions of a foot, which is used herein describe the non-static positioning and movement of a foot during walking, running, jumping, etc.

To avoid any misunderstanding, the word "pressure" as used herein is pressure in the mechanical sense meaning "force per unit area". Generally, the human body only perceives and is affected by pressure differences. An example of a pressure differential is a barefooted person bringing a heel down on a pebble or a hard flat surface. In this event, a substantial portion of the person's weight will be concentrated at the contact area between the pebble and the foot, and the resultant extreme pressure differential will cause pain and potential trauma. Thus, the shape and mechanical nature of objects forced together determines the pressure distribution between the objects. In the instance of two rigid objects, computation of the pressure is simple because the contact areas are constant. In the instance of two resilient objects, the issue is much more complex due to increased force causing an increase in the contact area. The human foot is a resilient object, and so is most footwear. Yet, the shapes of both when loaded determine the distribution of pressure between the two. If the shape of either is changed, then the pressure distribution changes. Hence, there is a direct, but complex, correlation between loaded shoe and foot shapes and pressure distribution.

The method of the present invention deals directly with the pressure distribution pattern on the plantar surface of the foot during ambulation to generate an inlay shape which redistributes pressures to a more advantageous pattern. The inlay shape is a mathematical function of the measured pressure distribution during ambulation, the desired pressure distribution, and the shape of the footwear.

Generation of a desired pressure distribution pattern is thus a necessary prerequisite to inlay shape generation. Although usually unexpressed, redistribution of pressure is the goal of any inlay fabrication method. With the method of the present invention, development of a desired pressure distribution follows receipt and analysis of all aspects of the measurement data by use of analysis tools which are essential parts of the system. These analysis tools may include, but are not limited to, displays of, a frame by frame view of the direct measurement data, a force versus time plot for each foot fall, a centroid of forces track for each foot fall, and composites, averages, and derivatives of each and all of the above. However, the fundamental element of the method of the present invention is pressure redistribution to reduce peak pressures through modification of the inlay shape, and underlying this is a computer routine to achieve pressure leveling within user-defined areas of the plantar surface of the foot.

Pressure leveling is achieved by increasing the inlay thickness in areas of low measured pressure. Conversely, the inlay is thinner in areas of greater measured pressure. At peak measured pressure areas, the inlay has a minimum thickness. The bottom shape of the inlay must reasonably fit, or match, the footwear. The top shape, or elevation (ST) at any single point is:

$$S_T = S_B + D - C \times T \qquad 1.0$$

where:

$S_B$ is the elevation of the bottom of the inlay

D is the desired pressure

C is the composite pressure pattern

T is the translation factor

Note that elevation is a vertical distance from a datum plane. "T" is empirically derived. The above may only be applied to local areas having uniform load bearing capability. Different areas of the foot have different capabilities. For example, the instep cannot tolerate as much pressure as the heel. Consequently, the total plantar surface area of the foot must be subdivided into appropriate local areas and 1.0 above must be applied with different "T" factors for each area.

Because the above can change the relative position of the skeletal elements of the foot, an additional elevation factor is necessary.

$$S_T = S_B + D - C \times T + P \qquad 1.1$$

where:

P is an added, or subtracted, depth

Note that the "P" factor varies between local areas.

The "P" factor can serve another important function in defining the shape of the inlay. It is an appropriate variable to accomplish adjustments to the foot's posture when a review of the measurement data as described above indicates such to be necessary. An example of this is a fallen metatarsal arch. In this instance, a high pressure is seen proximal to the second through fourth metatarsal heads. Without an appropriate "P" factor adjustment to this local area, an inappropriate inlay shape could result.

Once the inlay shape is determined, the numeric specification can be used to control automated equipment to fabricate the inlay. The ideal material for inlay fabrication must be resilient to some degree. If the inlay is to be fabricated by machining, it is preferably machined on all sides. Consequently, the present invention includes a means to support all inlay material blank pieces on all six sides and a sequence of milling to assure maximum stability of the work piece, maximize efficiency of debris removal, and achieve adequate precision.

The advantages of the method of the present invention include but are not limited to reduced space requirements for data collection and fabrication, objective measurement capability to minimize guesswork, increased speed of fabrication, and the elimination of most of the hand work mess, and clutter of traditional custom inlay fabrication. Further, manipulation of the inlay shape prior to fabrication, evaluation of shape and data files either locally or at a remote location, the capability to collect data for research purposes, and post-fit pressure analysis is provided. Additionally another significant advantage is that it allows the Fabricator to directly observe, manage, adjust, and work with a desired pressure distribution as a means of creating an inlay shape prior to actual fabrication.

Thus, in one aspect of the present invention, a method for fabricating an orthotic inlay for insertion into footwear is provided, comprising:

obtaining force data which is indicative of the magnitude and distribution of forces present on the plantar surface of a foot during ambulatory functions;

generating optimum orthotic shape inlay data based on said force data; and fabricating said orthotic inlay using said orthotic inlay shape data.

DETAILED DESCRIPTION OF THE DRAWINGS

DETAILED DESCRIPTION OF THE INVENTION

A method for fabricating a custom designed orthotic inlay using force and measure data present on a user's foot is provided herein. In general, the process includes three major steps. These include data collection, inlay shape generation, and inlay fabrication. All of these activities are performed and/or supervised by an inlay fabrication machine through the use of an inlay software package as described herein.

In general, the process is first used to measure the distribution of pressure on the foot when the subject individual is standing, walking, running, etc. This is done using an intra-footwear pressure distribution measurement system or device which interferes as little as possible with the subject's movements. This body of data is then converted to digital form and transferred to a computer system or other form of central processing unit (CPU). The computer system then functions as an analysis tool for operator review of the body of data. The computer system also functions to generate an inlay shape through software routines controlled by user input. The result of this is an inlay shape defined by a digital shape file. This shape information is then the basis for other software to control an inlay fabrication machine.

Figure 1:
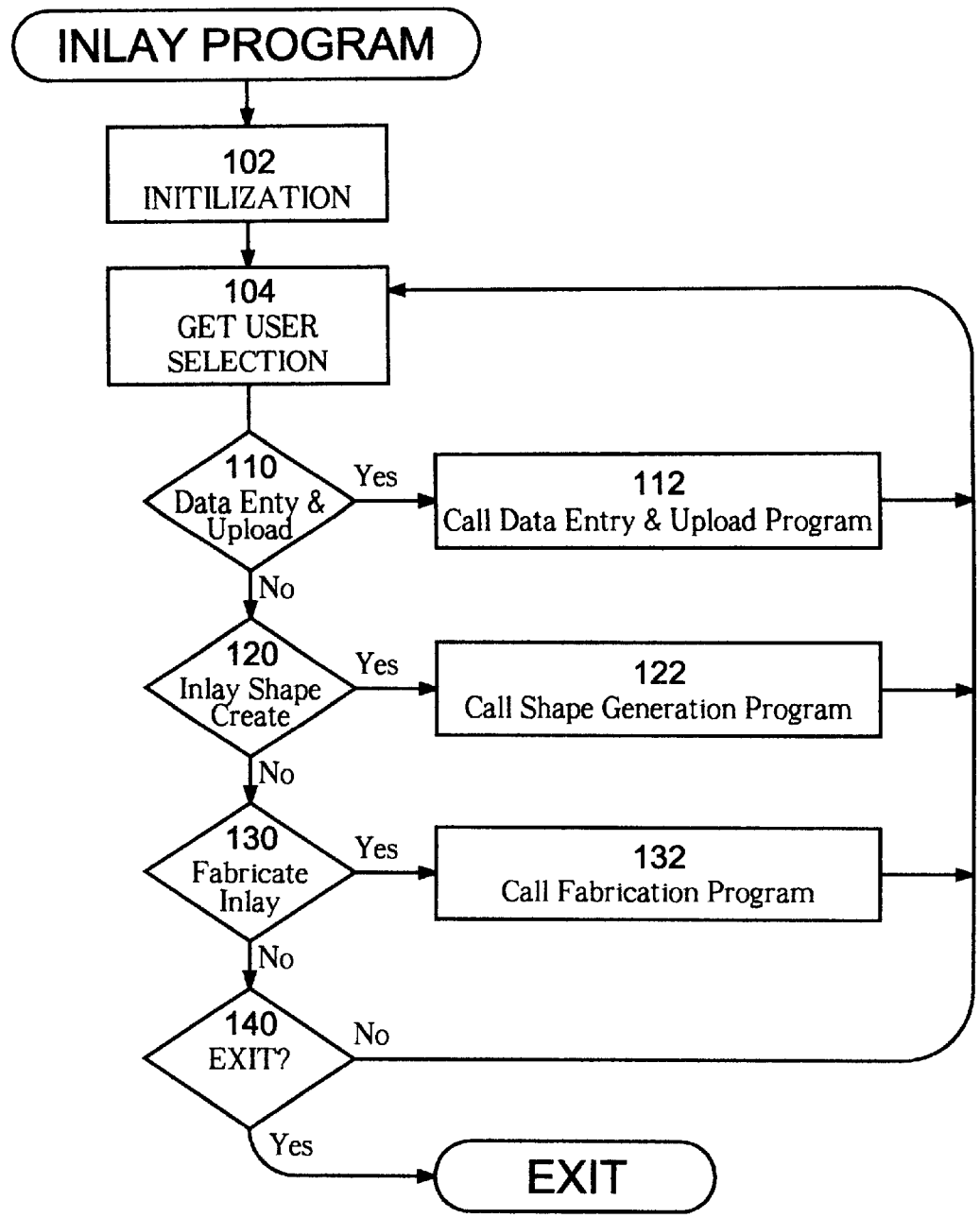
FIG. 1 is a flowchart of a process used to size and fabricate an orthotic inlay.

Referring now to FIG. 1, a flow chart of the main inlay program is shown. This program serves only as a user entry point to the fabrication system. Step 102 is a routine necessary to any software program for the allocation of memory, opening of files, computer screen displays, etc. Step 104 allows the user to select one of the three aforementioned steps as well as other programs not shown on the flow chart of FIG. 1. Step 110 is a test for user selection of the function of step 112, step 120 is a test for user selection of the function of step 122, step 130 is a test for user selection of the function of step 132, and step 140 is a test for user selection to exit the program. If all of the tests of steps 110, 120, 130, and 140 are false, program activity continues with step 104. If any of steps 112, 122, or 132 are executed, program activity continues with step 104 upon return from any of these programs.

The first major process step is a means for obtaining measurement data. This is necessary component, but not a required step of the present invention since different methods and apparatus can be utilized to obtain the force and pressure distribution data necessary to operate the orthotic inlay fabrication machine. Preferably, a means is provided for receiving this measurement data, collecting essential non measurement data pertainment to the fabrication technician's analysis, and to link the measurement data with the individual. Such non-measurement data may include but is not limited to a subject's name, age, general health, date of measurement, and type of footwear. The essential criteria for this body of pressure measurement data is that a) it must be reasonably accurate; b) it must consist of individual pressure values taken at known locations across the entire plantar foot surface closely spaced with respect to the size of the parts of the human foot anatomy; c) it must include multiple measurements of the total of all locations taken at a rate to assure multiple measurements of all locations for each foot fall; d)

it must represent pressures between the plantar foot surface and the inside surface of the subject's footwear; and e) must be taken while the subject is engaged in unrestrained ambulation. Although not a specific part of any major activity, coordination between the various programs to capture and convey aspects of size and shape of the preferred footwear and the location with respect to the footwear of each of the pressure measurement points is also essential for the accuracy of the present system.

Although the forces typically measured in the present invention are forces acting vertically on the sensor arrays, it is possible to also measure "translational forces" which act in a non-vertical direction. Pressure distribution measurements are generally made with sensor arrays having individual sensors which cannot distinguish force vectors. In fact, it is often advantageous to construct sensors which do not respond to horizontal components. However, inferences can be drawn with respect to horizontal forces when the entirety of the vertical forces acting on the foot are considered as a whole and in conjunction with the mechanical characteristics of the foot anatomy and the footwear.

Figure 2:
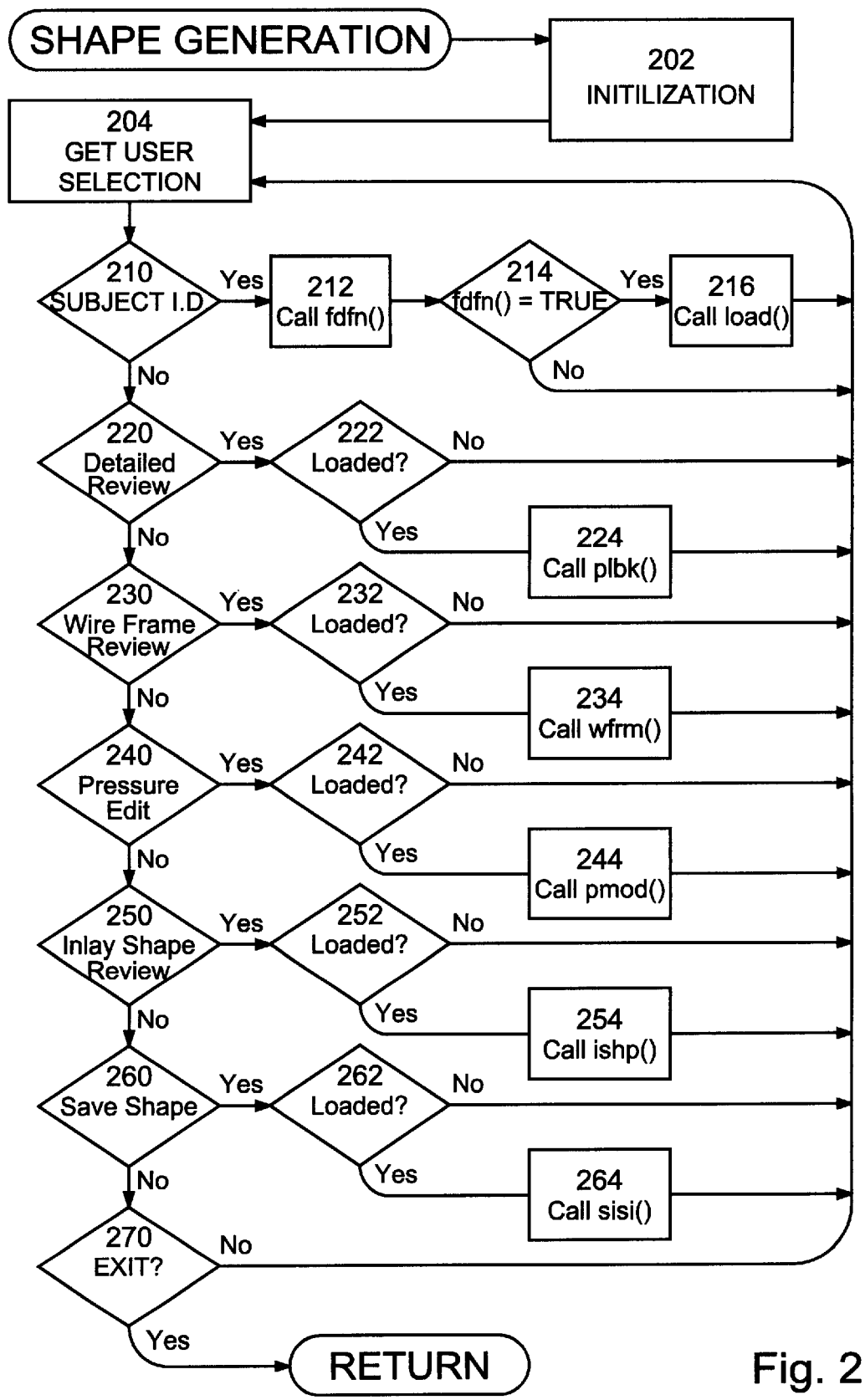
FIG. 2 is a flowchart of an inlay shape generation program.

The second critical process is shape generation. Referring now to FIG. 2, a flow chart is provided of the shape generation program. Step 202 is a routine necessary to any software program for the allocation of memory, opening of files, computer screen displays, etc. User settings are stored in permanent data storage files for consistency between program runs. A file which can optionally contain a comprehensive history of the program activity is also maintained. This file is rewritten for each program invocation. At a minimum, it will include a text message giving the reason for the last program termination. This step 202 also includes all data storage specifications. Significant data storage specifications include a series of two vector short integer arrays, sized 54 by 120, to receive and manipulate pressure measurement data and another series of short integer arrays, sized 120 by 112, are used in the process of generating the inlay shape.

Step 204 is a simple menu routine to receive user input.

Figure 3:
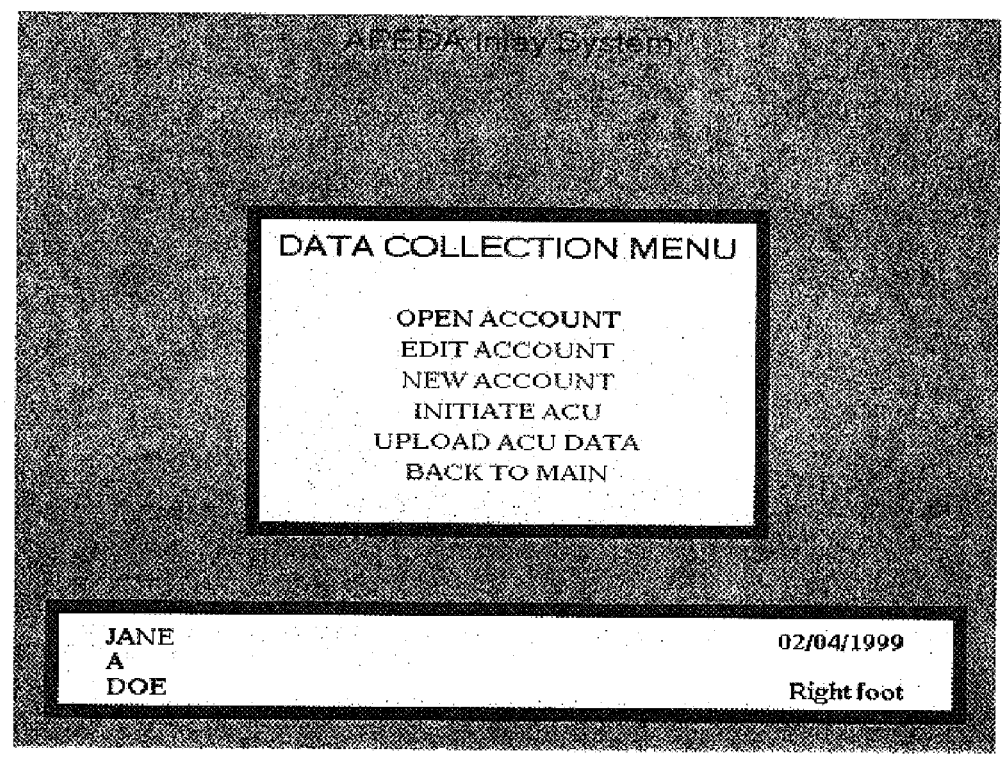
FIG. 3 is a view of a computer monitor display showing an interactive user display.

Step 210 tests for a user command to select an existing measurement data file. If Step 210 is true, step 212 is executed to allow the user to review a list of available measurement data files. Upon exit from step 212, step 214 is executed to test for user selection of a measurement data file. If step 214 is true, step 216 is executed, else step 204 is executed. Step 216 loads the selected measurement data file. Upon exit from step 216, the program returns to step 204. Note that until step 216 is successfully executed, steps 222, 232, 242, 252, and 262 will always test false. FIG. 3 shows the appearance of the screen on initial entry into step 216.

Figure 4:
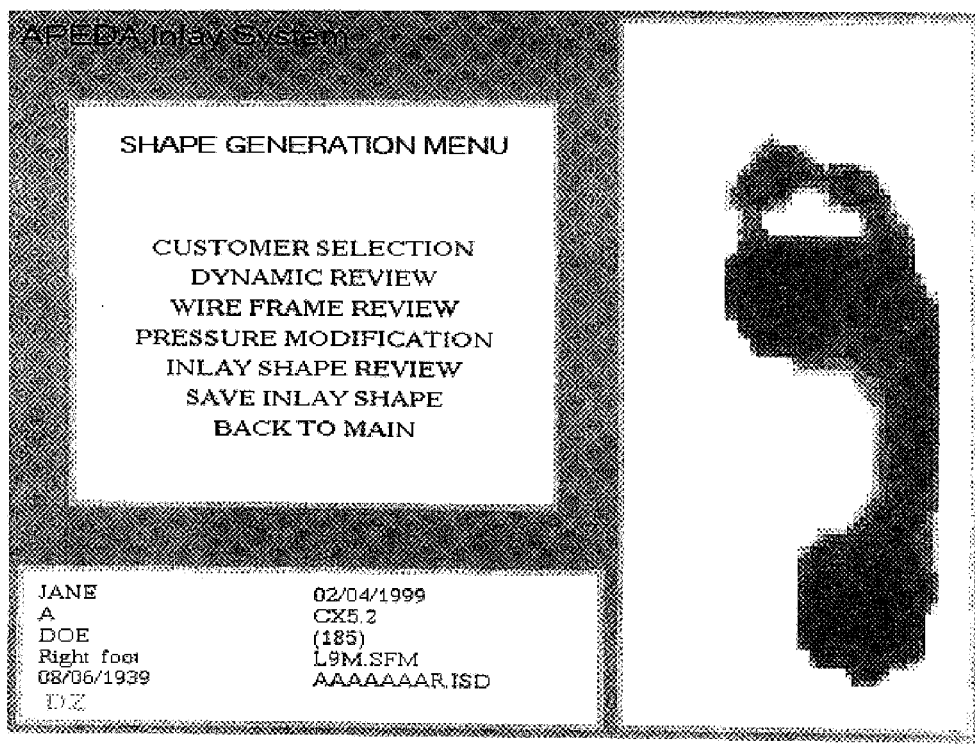
FIG. 4 is a view of the computer monitor of FIG. 3 with illustrative example data.

Step 216 functions to first open the selected measurement data file and read the entire file into a buffer. In addition to the actual measurement data, this buffer then contains additional pertainment information including the subject's name and address, date of measurement, identification of footwear, etc. The "load" function of step 216 also calls other routines to load a footwear shape file and a file containing a list of coordinate locations for each pressure measurement point. This is followed by calling another routine (savg) to repetitively search through the measurement data buffer and extract all reads of a single sensor, load these into each eighth element of another buffer, and then apply an interpolation routine to logically generate values for the intermediate points. Each point intermediate to these eighth points is set equal to seven times the sum of the two adjacent eighth data points less the sum of the two next adjacent eighth data points divided by 12. This procedure is repeated twice more to evaluate the intermediate points to the fourth points and the intermediate points to the second points. Any resultant value less than zero is set to zero. The result of this procedure is a pressure versus time plot typified by FIG. 5. Each measurement point is then evaluated as a factored average of its peak values and stored in its respective location in the "commap" 54 by 120 vector data array. The "load" routine next calls "dfil" routine which functions to evaluate intermediate locations in the "commap" array by using a similar interpolation routine. On completion, a composite numeric pressure distribution pattern representative of all foot falls is complete. FIG. 4 shows the appearance of the computer display at the completion of step 216, and depicting the force and pressure distribution present on the planar surface of the subject's foot who is identified as Jane A. Doe.

Figure 6:
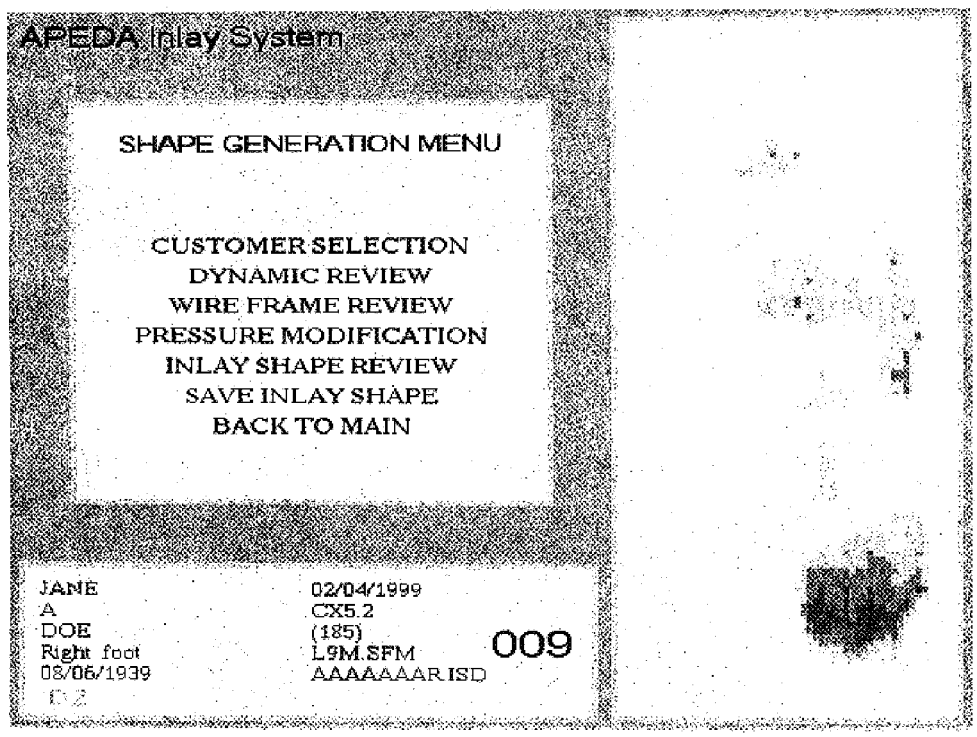
FIG. 6 is a depiction of the pressure distribution on the bottom of a foot, and indicating a particular frame of measurement.

Step 220 tests for a user command to do a detailed frame by frame review of the pressure distribution measurement data. If true, and if step 222 is also true, step 224 is executed and "plbk" routine is called. A typical computer display during this activity is shown by FIG. 6., and which identifies the pressure distribution pattern for the pattern of FIG. 4.

Figure 7:
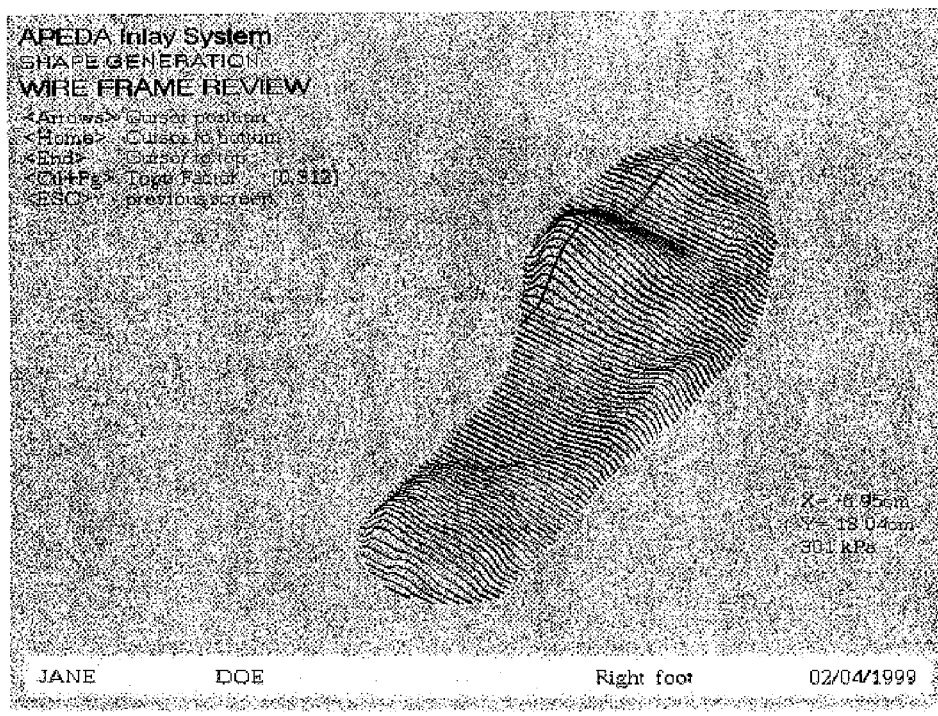
FIG. 7 is a wire frame isometric view showing the distribution of pressure on a user's foot.

Step 230 tests for a user command for a wire frame review of the composite pressure distribution pattern. If true, and if step 232 is also true, step 234 is executed and a "wfrm" routine is called. A typical computer display is shown in FIG. 7 which shows a wire frame review of the force and pressure distribution.

Figure 8:
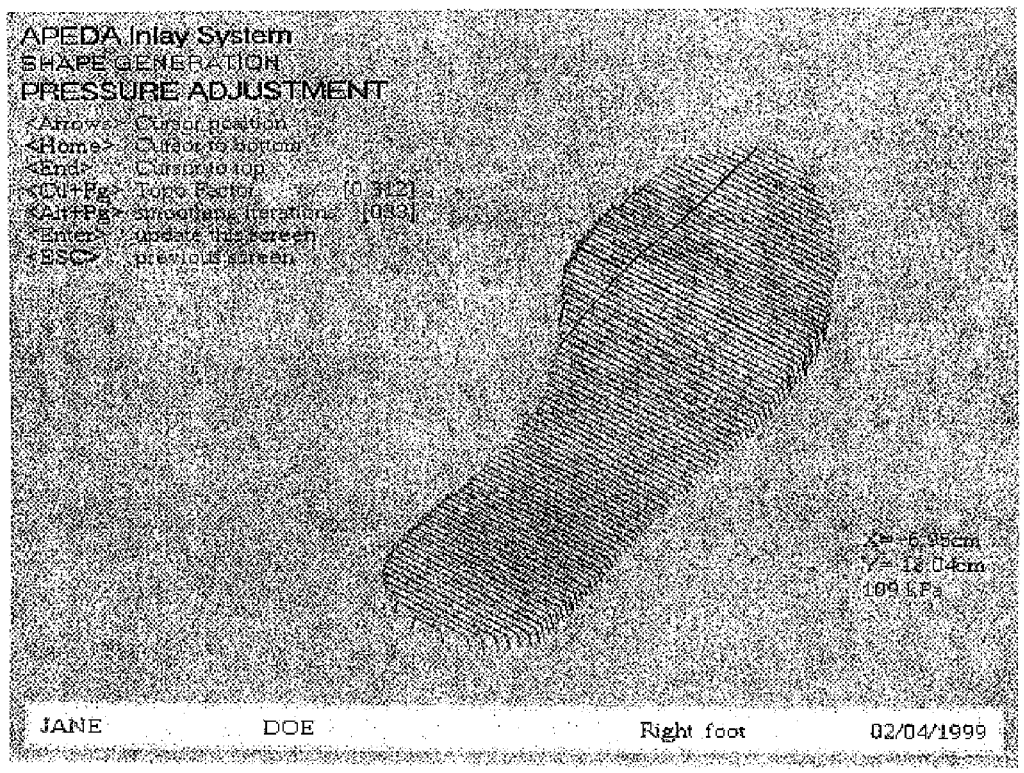
FIG. 8 is an isometric view of a desired pressure pattern.

Step 240 tests for a user command for pressure modification routine. If true, and if step 242 is also true, step 244 is executed and a "pmod" routine is called. A typical computer display is shown in FIG. 8, which identifies an isometric view of the desired pressure pattern. In FIG. 8, the cursor remains at the same coordinates as in FIG. 7.

Figure 9:
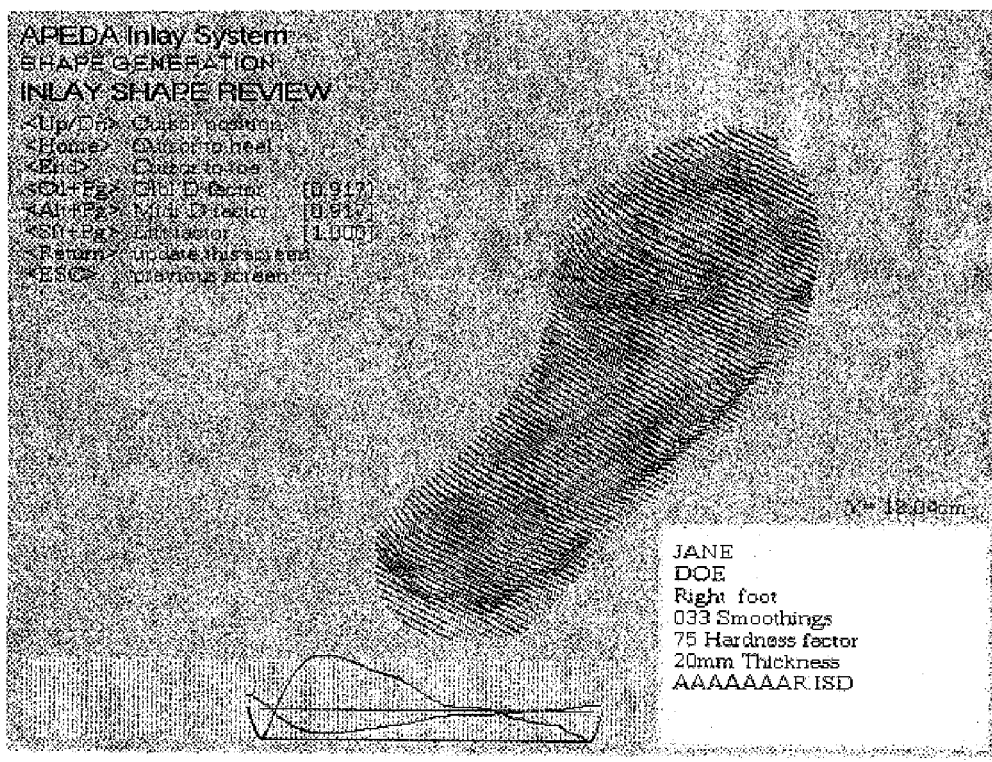
FIG. 9 is an isometric view of the top and bottom of the inlay shape generated from the two patterns shown in FIG. 7 and FIG. 8.

Step 250 tests for a user command for a review of the inlay shape. If true, and if step 252 is also true, step 254 is executed and the "ishp" routine is called. A typical computer display is shown by FIG. 9. In FIG. 9, which more clearly depicts an isometric view of the top and bottom of the inlay shape generated from the two previous patterns of FIG. 7 and FIG. 8. The Y axis cursor remains at the same location.

Step 260 tests for a user command for to save the inlay shape created by step 254. If true, and if step 262 is also true, step 264 is called and the "sisi" routine is called. The sisi routine (Save Inlay Shape Information) first creates a unique file name for the inlay shape information file, saves this information, and then records the file name in the pressure measurement data file to link the two files. Step 270 tests for a user command to exit the shape generation program. If true, activity continues within the calling routine.

Referring now to FIG. 3, the upper left box contains the menu for the shape generation routine. The "OPEN ACCOUNT" option is highlighted. The user can change the highlighted option by pressing the "up" or "down" keys, and when the "enter" key is pressed, the highlighted option is executed.

Referring now to FIG. 4, the box at the bottom of this screen contains the subject's name and other incidental information. The box at the right is a 12 color representation of the composite pressure distribution pattern. The background is preferably black, while minimum pressure is represented by dark blue, maximum pressure is in bright red, and intermediate pressures are green shades. Of course, any variety or combination of colors may be used to show the pressure distribution pattern. There are preferably 12 pressure ranges represented by the various colors.

Figure 5:
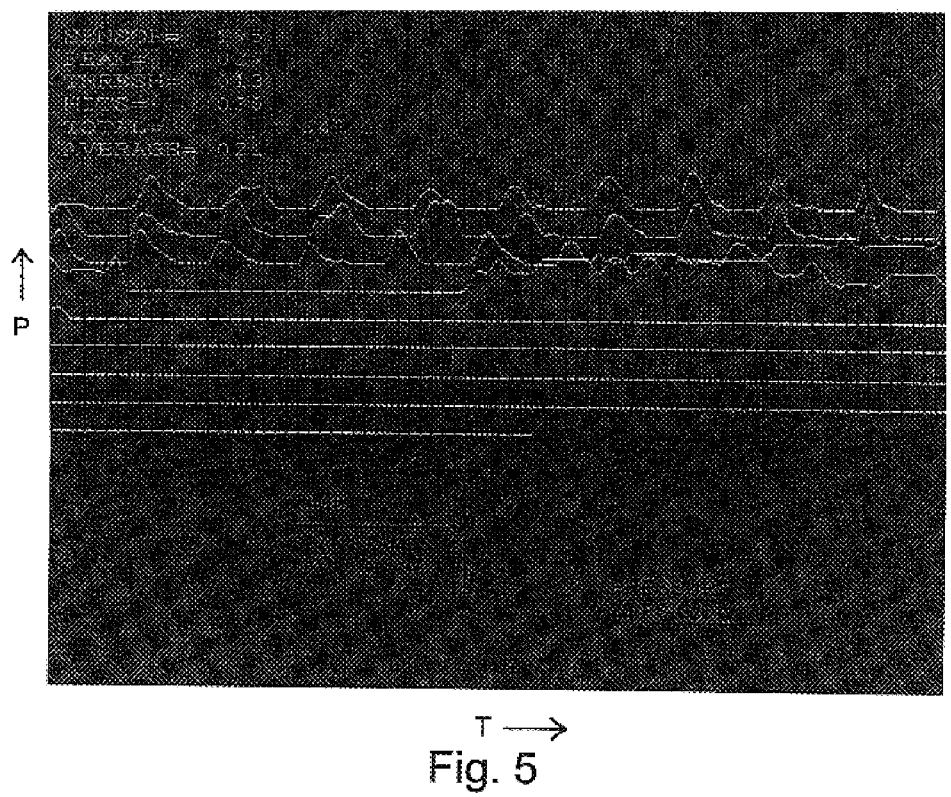
FIG. 5 is a plot of pressure v. time.

Referring now to FIG. 5, this is a screen for technical analysis only, and is not ordinarily seen by the user. Color of each line of the traces is different to facilitate review when overlapping occurs. The top three lines show repeated footfalls on a single sensor identified by the first line of text at the top. The right half of the fourth line shows the subject attempting to stand still on one foot. The remaining flat lines indicate only the buffer in the pressure measurement device which was not completely filled. Time is constant throughout the trace. Note that during the walking portion, this sensor is loaded slightly more than half of the time. For this sensor, the highest peak measured is 65 (PSI). There are 26 instances of peak pressures above the threshold value of 32. The total of these peak pressures is 1167 and the average pressure value is 44. This is the pressure used in the composite pressure distribution pattern. It should be kept in mind that, although the pressure distribution can be changed, the total force on the foot due to body weight and ambulation dynamics cannot be changed by any aspect of footwear. Also, the composite pressure distribution pattern represents a total force greater than any actual force imposed by the subject. This is because the person's total weight is typically supported first by the heel area and then by the forefoot area while the composite pressure pattern generation algorithm necessarily focuses on peak pressures at each measurement point. In order to generate the inlay shape, a conservation of force concept can be applied to sub-areas of the plantar surface of the foot once the total force to be, or is being, supported by the sub-area is determined.

Referring now to FIG. 5, this is a screen for technical analysis only, and is not ordinarily seen by the user. The color of each line of the traces is different to facilitate review when overlapping occurs. The top three lines show repeated footfalls on a single sensor identified by numbers in the first line of text at the top. The right half of the fourth trace line shows the subject attempting to stand still on one foot. The remaining flat lines indicate only that the buffer in the pressure measurement device was not completely filled. Time is constant throughout the trace. Note that during the walking portion, this sensor is loaded slightly more than half of the time. For this sensor, the highest peak measured is 27 psi. There are 30 instances of peak pressures above the threshold value of 13. The total of these peak pressures is 641 and the average pressure value is 21. Thus 21 psig is the pressure used in the composite pressure distribution pattern. It should be kept in mind that, although the pressure distribution can be changed, the total force on the foot due to body weight and ambulation dynamics cannot be changed by any aspect of footwear. Also, the composite pressure distribution pattern represents a total force greater than any actual force imposed by the subject. This is because the person's total weight is typically supported first by the heel area and then by the forefoot area while the composite pressure pattern generation algorithm necessarily focuses on peak pressures at each measurement point. In order to generate the inlay shape, a conservation of force concept can be applied to sub-areas of the plantar surface of the foot once the total force to be, or is being, supported by the sub-area is determined.

Referring now to FIG. 6, the "001" at the right of the bottom box indicates this is the first frame. The right box shows the same color coded pressure distribution pattern as for the composite pattern of FIG. 4. In this instance, the subject's foot is just coming into contact with the ground. There is light pressure at the heel, and less at the forefoot area. Some of the pressure evident in this display, particularly in the mid-foot area, is residual and results only from the footwear being held snugly to the foot. The user moves from frame to frame by use of the arrow keys on the keyboard. The result is essentially a motion picture of the measured pressure distribution patterns on a users' foot.

Referring now to FIG. 7, the image in the center of the screen is an isometric view of the composite pressure distribution pattern. All edge pressures are zero, and upward displacements indicate increasing (positive) pressure. There are no negative pressures. The dark lines crossing at the first metatarsal head are a cursor. The cursor can be moved in four directions by use of the arrow keys. Below and to the right of the wire frame are three text lines indicating the location of the cursor and the pressure at the cursor. These are in standard medical terms of centimeters and kilopascals with the coordinate origin at the lateral posterior edge of the pattern. This particular individual has an extremely high arch. Note the absence of pressure at the medial mid-foot. The elongated pressure area at the fifth metatarsal is probably due indirectly to poorly fitting footwear. Note that the pressure at the cursor is 301 kilopascals as shown in the lower right hand portion of the FIG. 7. It is important to remember that this image depicts the pressure on the bottom of a foot, and regardless of the similarity, does not depict the shape of the foot.

Referring now to FIG. 8, the image at the center of the screen is an isometric view of the desired pressure pattern. As in FIG. 7, all edge pressures are zero, but rise abruptly to constant peak pressure. Initially, each cross section is equal in area to its counterpart in the composite pressure distribution pattern of FIG. 7. The desired pressure distribution pattern of FIG. 8 is derived from these initial cross sections in a manner that the total cross sectional area of all sections in the pattern of FIG. 8 is equal to the total cross sectional area of all sections in the pattern of FIG. 7. Note that the cursor position is the same in FIG. 8 as it is in FIG. 7, but the pressure at the cursor position is now 109 kilopascals. This is a significant reduction from the pressure at this point in the composite pressure distribution pattern of FIG. 7.

Referring now to FIG. 9, the image at the center of the screen is an isometric view of the top and bottom of the inlay shape generated from the two previous patterns of FIG. 7 and FIG. 8. The moire effect is due to the superimposition of the two patterns. The bottom pattern depicts the inside shape of the footwear. This shape information is the output of a separate procedure and can be in any of a number of currently available methods to digitize, or express as numbers, the footwear shape. At the center bottom of FIG. 9 is a series of cross sectional lines depicting, from highest to lowest, the measured pressure, the desired pressure, the top of the inlay shape, and the bottom of the inlay shape. The vertical scale of the pressures is arbitrary. The vertical scale of the inlay shape is one to one with the actual inlay shape being developed. The thickness of the inlay at each point is computed by subtracting the measured pressure from the desired pressure and multiplying the result by a factor. The user input settings for global depth factor, mid-foot depth factor, and lift factor are shown at the upper left of FIG. 9. The Global depth factor affects the entire foot area and the mid-foot depth factor affects only the mid-foot area. The lift factor does not affect cross sectional inlay thickness. A positive lift factor increases the total depth of the inlay at the heel and may reduce it at the toe. A negative lift factor does the opposite. Lift is used when deemed appropriate by the user.

The third major process step in the present invention is to fabricate the inlay using the numeric shape information generated by the second activity. In summary, the method of the present invention is to mill or machine all inlays from a standard size blank piece of suitable material. This involves cutting a pliant material on all six sides. Preferably the pliant inlay material is comprised of plastic, forms, (open and closed cell), ethyl vinyl acetate (EVA) or other similar materials known in the art. This pliant material can be any material having the preferred mechanical characteristics. The preferred mechanical characteristics are flexibility similar to that of a shoe sole, a small amount of compressibility, and light weight. The most obvious material is a closed cell, high weight, polymer foam.

The milling equipment and disclosed method of use is designed to support the work piece on all six sides. Referring now more specifically to FIGS. 10–16, the work piece is held in opening 356 and formed by holding frame 350 and on the two remaining sides by each of the plates 450. Plates 450 are stationary, holding frame 350 moves up and down to form an "X" motion, carrier 400 moves left and right to form a "Y" motion, and mill heads 430 each move forward and backward to form "Z1" and "Z2" motions. The long slot 452 in plates 450 is for access to the work piece by the cutting bits 438.

Figure 10:
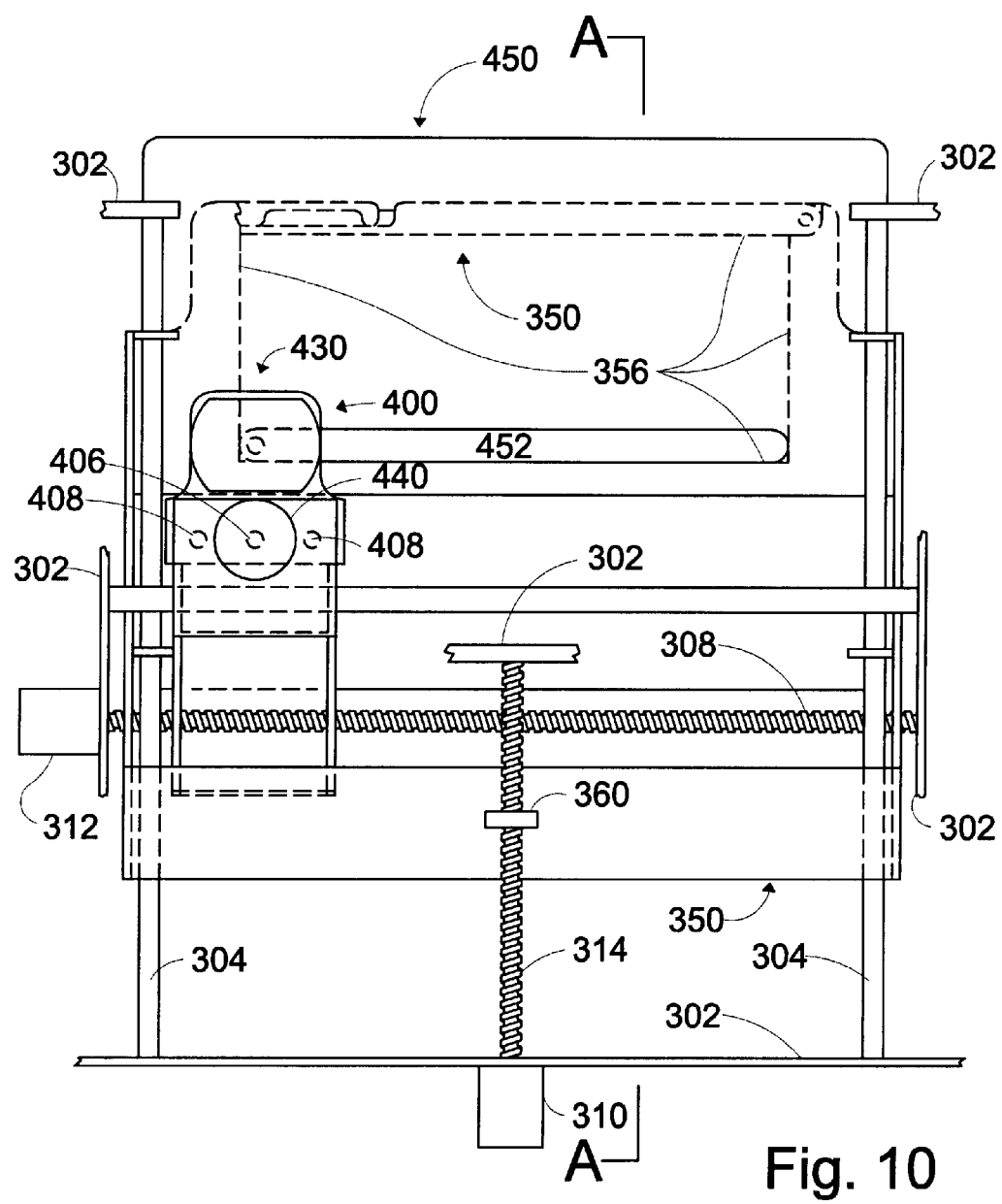
FIG. 10 is a front elevation view of an inlay fabrication machine.

Referring now to FIG. 10, which is a frontal view of the assembled machine, Chassis 302 is not shown in its entirety, but is a single element necessary to support all other parts. Motor 310 drives the "X" motion, motor 312 drives the "Y" motion, and motors 440 drive the "Z" motions. Guide rails 304 support the "X" motion, guide rails 306 support the "Y" motion, and guide rails 408 support both "Z" motions. Motors for all motions turn drive screws 308, 314, and both of 406.

Figure 11:
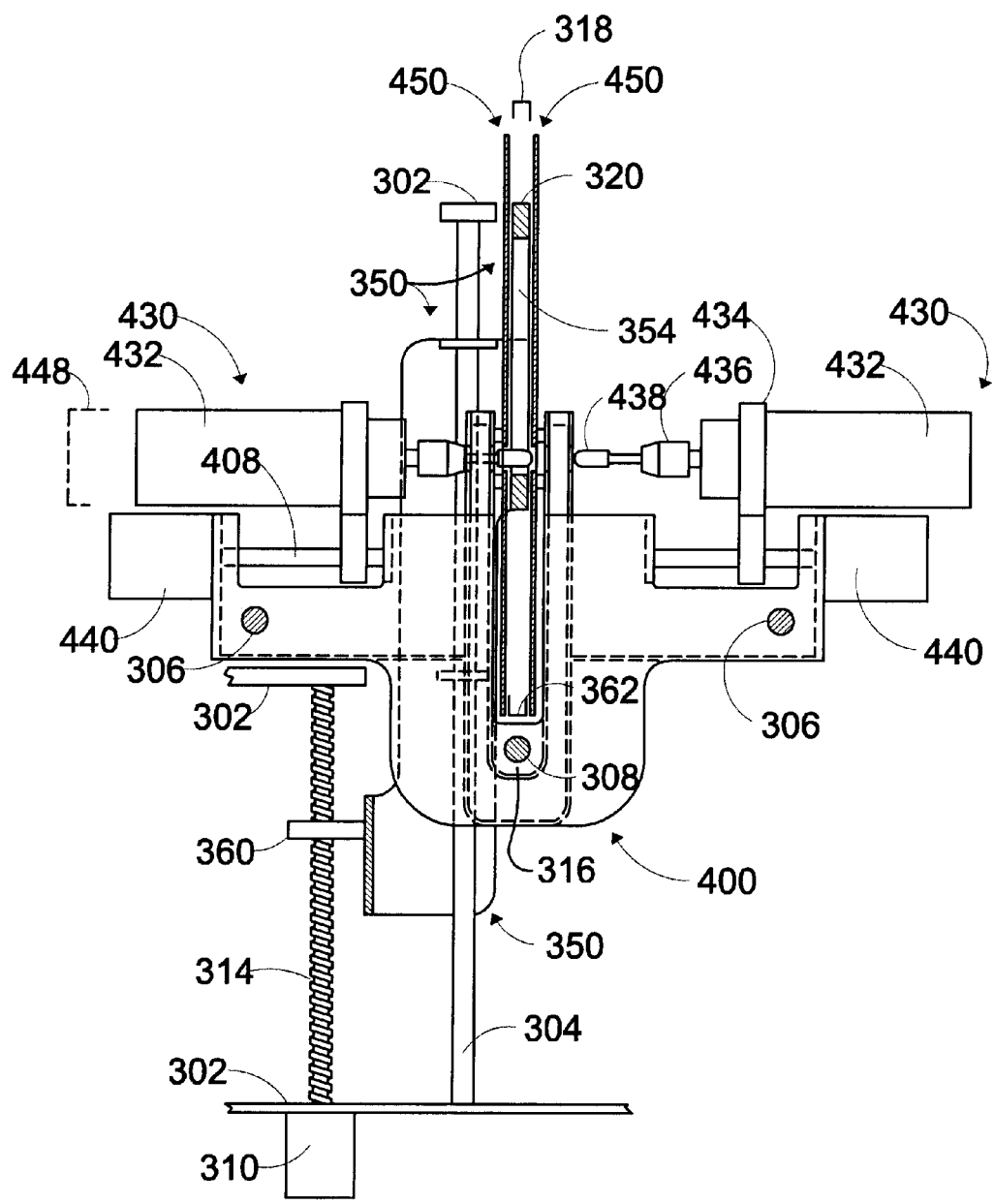
FIG. 11 is a side elevation view of the inlay fabrication machine shown in FIG. 10.

Referring now to FIG. 11, a side view of the assembled machine is provided herein. The asymmetry or offset of frame 350 is necessary to preclude interference with carrier 400. Part 400 extends around the bottom of fixed plates 450 and the lowest position of frame edge 362. Position 318 is the highest position of frame edge 354 which is used for material insertion and removal. Position 320 is the highest position of frame edge 354 during milling. Mill head motors 432 are identical, and have one direction of rotation. Thus if cutting bits 438 were to meet when running, damage would occur. This situation is prevented by arms attached to both sides of mounting brackets 434 and extending under position 316 to prevent contact between cutting bits 438.

Figure 12:
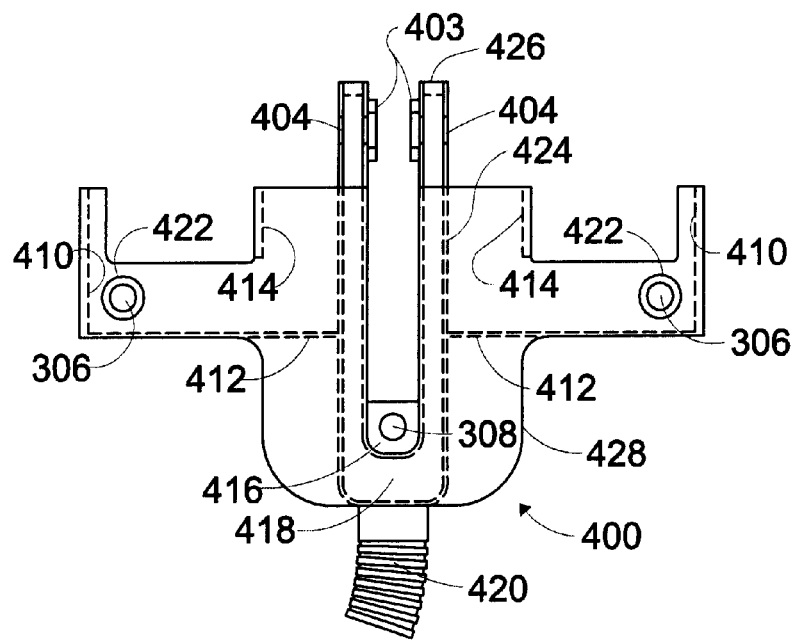
FIG. 12 is a detailed side view of a debris removal cowling.

Referring now to FIG. 12, which is a detailed side view of carrier 400 and FIG. 4 which is a detailed front view of the same carrier 400. Drive nut 416 transfers drive force from motor 312 to carrier 400. Bearings 422 slide along guide rails 306 and prevent undesired movement of carrier 400. Seals 403 contact and slide against plates 450. Parts 414 and 410 receive "Z" motion guides 408 and drive screws 406. Parts 410 also receive drive motors 440. Parts 412 are stiffeners. Holes 404 allow cutting bits 438 access to the work piece. Parts 424 and 426 are tightly connected to parts 428 to form air tight vacuum debris removal channel 418. Channel 418 communicates with flexible vacuum hose 420 leading to a vacuum debris collection system which is not shown.

Figure 13:
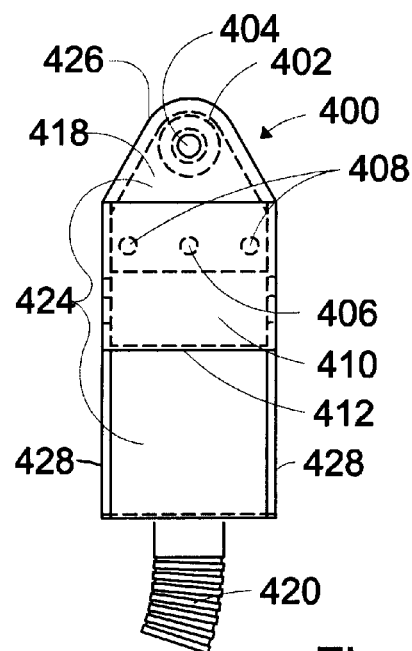
FIG. 13 is a is a front view of the cowling shown in of FIG. 12.

Referring now to FIG. 13, a front view of the cowling shown in FIG. 12 is provided herein and includes the components discussed above.

Figure 14:
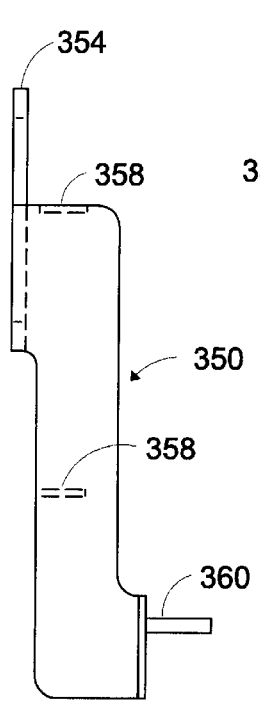
FIG. 14 is a detailed side elevation view of a holding frame.
Figure 15:
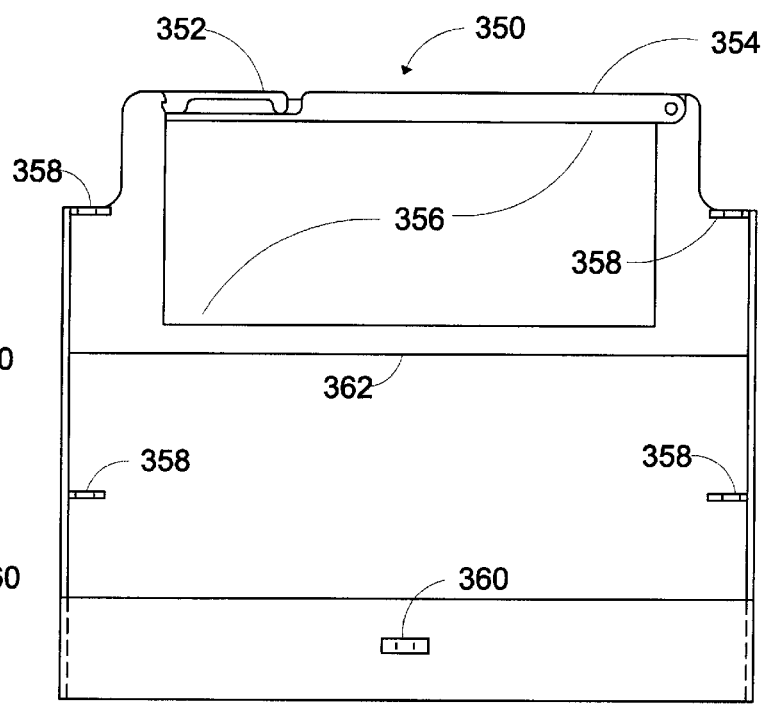
FIG. 15 is a detailed front elevation view of the holding frame shown in FIG. 14.

Referring now to FIG. 14, which is a detailed side view of holding frame 350 and FIG. 15 which is a detailed front view of the same holding frame 350. Drive nut 360 transfers drive force from motor 310 to holding frame 350. Bearings 358 slide along guide rails 304 and prevent undesired movement of holding frame 350. Latch 352 holds frame edge 354 in place during milling and can be released by hand to swing up frame edge 354 for insertion or removal the work piece.

Referring now to FIG. 15, a detailed front elevation view of the holding frame shown in FIG. 14, and including the various components described therein.

Figure 16:
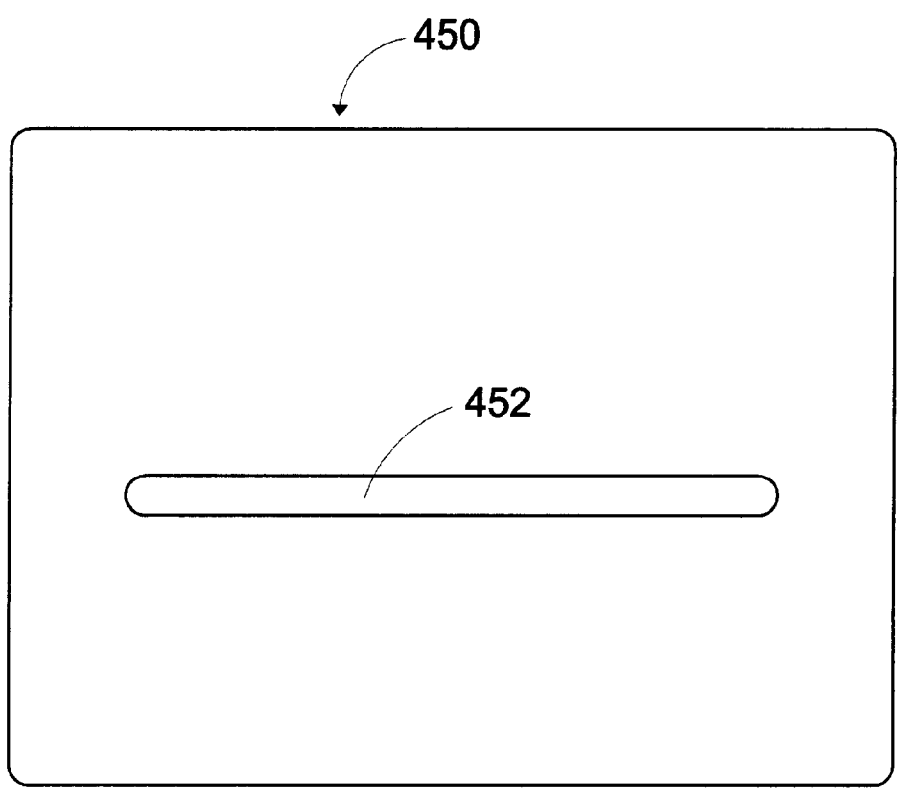
FIG. 16 is a front elevation view of plates used to hold the work piece, the slot representing a location where a cutting instrument extends therethrough.

Referring now to FIG. 16, a front elevation view of one of the plates 450 is shown. These plates 450 are fixed directly to chassis 302. The plates 450 are separated by the thickness of the work piece. Different thicknesses of work pieces can be accommodated by repositioning plates 350 and using thinner or thicker seals 402. Note that this machine can easily be adapted for automated work piece feeding, and all dimensions, materials, thicknesses, etc. are subject to engineering analysis and modifications. The particular arrangement described herein is optimized for compactness. Other optimizations may be advantageous depending on circumstances.

The necessary components of wiring, limit switches, encoders, motor driver units, indexer facility, etc. are not necessarily part of the present invention and are not described herein. However, as appreciated by one skilled in the art, most of these components are off-the-shelf items used frequently in the mechanical and electrical arts. In a similar manner, tool path generation software is necessary, but it is not part of the present invention and is not described herein.

The foregoing description of the present invention has been presented for purposes of illustration and description. Furthermore, the description is not intended to limit the invention form disclosed herein. Consequently, variations and modification is commensurate with the above teachings, and the skill or knowledge of the relevant art, or within the scope of the present invention. The embodiments described hereinabove are further intended to explain best modes known for practicing the invention and to enable others skilled in the art to utilize the invention as such, or other embodiments and various modifications required by the particular application or use of the present invention. It is intended that the appended claims be construed to include alternative embodiments to the extend permitted by the prior art.

What is claimed is:

1. A method for making a custom shaped resilient orthotic inlay adapted for positioning below a user's foot based on plantar surface force measurements taken during subject ambulation, comprising:

utilizing force data which are indicative of the magnitude and distribution of forces present over a period of time on substantially the entire plantar surface of a foot during ambulatory functions and measured utilizing a specific shaped footwear worn by the user;

generating optimum orthotic shape inlay data based on said force data and a desired pressure distribution, and fabricating said orthotic inlay using said orthotic shape inlay data, said orthotic inlay having a distinct contoured shape on at least four distinct sides for redistributing pressure below a user's foot, and which is contoured to fit within the specific shaped footwear.

2. The process of claim 1, further comprising utilizing data related to a footwear shape to generate said optimum orthotic shape inlay data.

3. The process of claim 1, wherein said utilizing force data step comprises downloading said force data to a data storage means.

4. The method of claim 1, wherein said fabricating step comprises cutting and shaping a flexible orthotic inlay material on at least six distinct sides to create a shape adapted to be positioned between the plantar surface of a foot and a specific type of footwear.

5. The method of claim 1, wherein said orthotic inlay material is comprised of a pliable material capable of being resiliently compressed.

6. The method of claim 1, wherein said fabricating step is automatically performed on an inlay fabrication machine receiving computer generated instructions which contain said optimum orthotic shape inlay data.

7. The process of claim 1, wherein said orthotic shape inlay data is generated for a specific physical activity for each individual user.

8. The process of claim 1, wherein said generating optimum orthotic shape inlay data step further comprises considering the material characteristics of an orthotic inlay material prior to fabricating said orthotic inlay.

9. The process of claim 1, wherein said fabricating step further comprises determining an optimum thickness of an orthotic inlay material at a plurality of locations based on said utilizing force data step.

10. The process of claim 1, wherein said utilizing force data step further comprises determining a plurality of forces present on the plantar surface of the foot based on a distinct type of footwear worn during subject ambulation.

11. The process of claim 1, wherein said utilizing force data step comprises positioning a force sensor array inside a user's footwear and below the plantar surface of a foot.

12. A method for fabricating a custom shaped orthotic inlay adapted for positioning below a user's foot using force data indicative of both the magnitude and distribution of forces present on substantially an entire plantar surface of a foot during ambulation and measured over a distinct interval of time, comprising:

provide an automated inlay fabrication apparatus with a means for securely holding an orthotic inlay material and at least one cutting instrument;

providing a memory means;

providing a central processing unit;

providing a data input means;

providing a communications means which allows the transmission of information and instructions between said central processing unit and said automated inlay fabrication apparatus;

providing a formable resilient inlay material for use in said inlay fabrication apparatus;

utilizing the force data which is indicative of the magnitude and distribution of forces present on substantially an entire plantar surface of a foot measured during ambulatory functions in a specific shaped footwear worn by the user;

storing the force data in said memory means;

generating optimum shape inlay data with said central processing unit by utilizing the force data; and fabricating said orthotic inlay using the force data and said inlay material positioned on said automated inlay fabrication apparatus, wherein said inlay material is selectively contained with said at least one cutting instrument, and shaped on at least four distinct sides, wherein said orthotic inlay redistributes pressure when positioned below the plantar surface of a user's foot, and is adapted to fit within the specific shaped footwear worn by the user.

13. The method of claim 12, wherein said automated inlay fabrication apparatus further comprises a visual display means to review one or more parameters related to the operation of said automated inlay fabrication apparatus.

14. The method of claim 12, wherein said memory means comprises a computer hard drive.

15. The method of claim 12, wherein said data input means comprises an operator interface including at least one of a keyboard and a mouse.

16. The method of claim 12, wherein said communications means comprises a communications cable.

17. The method of claim 12, wherein said utilizing force data step comprises positioning a foot sensor array between the plantar surface of the foot and an interior surface of a footwear positioned on a user's foot, said foot sensor array having a plurality of row and column electrodes with intersections at a plurality of locations and which have a resistive material positioned between said rows and columns of electrodes at each of said intersections, wherein the magnitude, distribution and relative change of pressure applied at each of said intersections can be measured during ambulatory functions of a user's foot over a given period of time.

18. The method of claim 12, wherein said fabricating said orthotic inlay step comprises:

positioning said inlay material in said inlay fabrication apparatus in a predetermined position;

orienting said at least one cutting instrument with respect to said inlay material; and cutting said inlay material on at least six distinct sides based on operating instructions generated from said optimum shape inlay data, wherein said orthotic inlay is fabricated to define a contoured shape adapted for redistributing pressure below a user's foot.

19. A process for a computer assisted fabrication of a resilient orthotic inlay which is adapted for positioning below a user's foot, comprising the steps of:

a) measuring both the magnitude and distribution of forces on substantially the entire plantar surface of a foot during ambulatory functions over a period of time to obtain force distribution data, said measuring step further comprises obtaining said data utilizing a specific shaped footwear worn by the user;

b) utilizing said force distribution data in combination with information relating to a desired pressure distribution profile to create an optimum orthotic shape inlay data profile; and c) fabricating an orthotic inlay comprised of a substantially resilient material by shaping said substantially resilient material on at least four distinct sides into a predetermined shape on an automated inlay fabrication apparatus based on said orthotic shape inlay data profile, wherein said orthotic inlay can be positioned below the plantar surface of a user's foot to redistribute pressure and which is contoured to fit within the specific type of footwear worn by the user.

20. The process of claim 19, wherein a thickness of said substantially resilient material for said orthotic inlay is determined at a plurality of locations based on said force distribution data and an intended purpose of use.

21. The process of claim 19, wherein said automated inlay fabrication apparatus is operated by a computer numeric control system in operable communication with a central processing unit.

22. The process of claim 19, wherein said automated inlay fabrication apparatus is capable of shaping said substantially resilient material in three distinct directions.

23. The process of claim 19, wherein said substantially resilient material is compressible.

24. The process of claim 11, wherein the user's footwear is comprised of at least one of a shoe, a sock, a boot, and a slipper.

* * * * *